(12) United States Patent
Davis et al.

(10) Patent No.: US 6,964,197 B2
(45) Date of Patent: Nov. 15, 2005

(54) SHELF LIFE TESTING UNIT

(75) Inventors: Craig P. Davis, Atlanta, GA (US); Stephen C. Ramey, Midville, GA (US); Mary L. Hughes-Olson, Mableton, GA (US); Edward R. Roberts, Douglasville, GA (US); Mihaela Penescu, Decatur, GA (US)

(73) Assignee: Ball Corporation, Broomfield, CO (US)

( * ) Notice: Subject to any disclaimer, the term of this patent is extended or adjusted under 35 U.S.C. 154(b) by 553 days.

(21) Appl. No.: 10/240,853

(22) PCT Filed: Oct. 16, 2001

(86) PCT No.: PCT/US01/32205

§ 371 (c)(1),
(2), (4) Date: Oct. 3, 2002

(87) PCT Pub. No.: WO02/33378

PCT Pub. Date: Apr. 25, 2002

(65) Prior Publication Data

US 2004/0007072 A1 Jan. 15, 2004

Related U.S. Application Data

(60) Provisional application No. 60/241,057, filed on Oct. 17, 2000.

(51) Int. Cl.[7] .............................................. G01L 9/00
(52) U.S. Cl. .......................................... 73/700; 53/432
(58) Field of Search .................... 73/700, 701, 723, 73/749, 19.05, 23.27; 53/432

(56) References Cited

U.S. PATENT DOCUMENTS

| | | |
|---|---|---|
| 3,958,448 A | 5/1976 | Willis et al. |
| 4,019,370 A | 4/1977 | Allocco, Jr. |
| 4,047,422 A | 9/1977 | Lyssy |
| 4,089,208 A | 5/1978 | Franks et al. |
| 4,180,614 A | 12/1979 | Angelo et al. |
| 4,184,362 A | 1/1980 | Standley et al. |
| 4,327,574 A | 5/1982 | Alberghini et al. |
| 4,437,353 A | 3/1984 | Hamerlinck |
| 4,459,843 A | 7/1984 | Durham |
| 4,555,935 A | 12/1985 | Elert |
| 4,852,415 A | 8/1989 | Bogatzki et al. |
| 4,880,120 A | 11/1989 | Myers et al. |
| 4,926,681 A | 5/1990 | Fitzpatrick |
| 4,942,758 A | 7/1990 | Cofield |
| 5,025,657 A | 6/1991 | Schenk |
| 5,123,278 A | 6/1992 | McKittrick |
| 5,279,873 A | 1/1994 | Oike |

(Continued)

OTHER PUBLICATIONS

American Society for Testing and Materials, "Standard Test Method for Determining Gas Permeability Characteristics of Plastic Film and Sheeting." *ASTM Designation: D 1434—82 (Reapproved 1988)*, Conshohocken, Pennsylvania.

*Primary Examiner*—Edward Lefkowitz
*Assistant Examiner*—Andre Allen
(74) *Attorney, Agent, or Firm*—Brinks Hofer Gilson & Lione

(57) ABSTRACT

A testing apparatus for testing the level of retained gas at elevated pressure in plastic containers for carbonated beverages includes a manifold assembly for engaging the mouth of a test set of the containers. The apparatus additionally includes a gas supply for supplying a desired quantity of a selected gas to each container, the gas preferably helium. The apparatus further includes pressure measuring units for measuring the pressure in each container, and a data collection system coupled to the pressure measuring units for periodically collecting pressure data along with ambient temperature data as a function of time. The collected data can be analyzed to determine shelf life of the containers. Using helium, the shelf life determination can be accomplished in about $\frac{1}{7}^{th}$ the time of conventional shelf life tests.

20 Claims, 7 Drawing Sheets

U.S. PATENT DOCUMENTS

| | | |
|---|---|---|
| 5,497,654 A | 3/1996 | Lehmann |
| 5,600,996 A | 2/1997 | Witschi |
| 5,614,718 A | 3/1997 | Brace |
| 5,918,270 A | 6/1999 | Heuft |
| 6,125,613 A * | 10/2000 | Eberhardt et al. ............ 53/432 |
| 6,205,847 B1 | 3/2001 | Nomoto |
| 6,240,769 B1 | 6/2001 | Heuft |
| 6,308,556 B1 | 10/2001 | Sagi et al. |
| 6,345,527 B1 | 2/2002 | Lehmann |
| 6,347,545 B1 | 2/2002 | Osborn et al. |
| 6,422,063 B1 | 7/2002 | Anantheswaran et al. |

* cited by examiner

SHELF LIFE TESTING UNIT

This application claims the benefit of prov. application 60/241,059 filed on Oct. 17, 2000.

TECHNICAL FIELD

The present invention relates to apparatus for testing the level of retained carbon dioxide in containers, particularly plastic containers designed to hold carbonated beverages. The present invention particularly relates to improvements in methods and apparatus for performing shelf life testing for such containers.

BACKGROUND ART

A standard method for testing the shelf life of containers consist of introducing carbonated water into a set of containers and tightly capping the containers with a cap that includes a septum penetrable by a sharp needled valve. The pressure within each of the containers is periodically sampled, typically on a one-week periodic basis, with a needle type pressure gage through the cap septum. The indicated internal (gage) pressure is recorded and, using an industry standard conversion method (Zahm-Nagel, ASTM F 1115-95), the pressure is converted to volumes of $CO_2$. One volume of $CO_2$ is defined as the quantity of pure $CO_2$ required to raise the internal pressure of a container by one atmosphere (14.7 psig) at standard temperature and pressure. The typical starting carbonated soft drink $CO_2$ volume specification is 4.0 volumes where the $CO_2$ volumes are counted starting from 1 atmosphere absolute pressure (i.e. Volumes=Atmospheres(absolute)−1).

The standard acceptable shelf life for carbonated beverages is defined in ASTM F 1115-95 as that time during which the container retains at least 85% of the original 4 volumes of $CO_2$. Stated another way, it is the time necessary for 15% of the original 4 volumes of $CO_2$, or 0.6 volumes of $CO_2$, to diffuse through the container wall. Since the volume of the containers being tested does not change during the test, and the ambient temperature to which the containers are exposed is held essentially constant during the test, the 15% loss in $CO_2$ is detected by a 15% decrease in pressure. This method is manpower intensive as container internal pressures are very sensitive to room temperature fluctuations and accuracy is often compromised due to leaks by the $CO_2$ past cap seals and by septum penetration.

Some of the general aims of the present invention are to automate the testing, minimize temperature sensitivity, and eliminate physical measurement inaccuracies. A particular aim of the present invention is to develop an accelerated testing method to reduce testing times.

Disclosure of Invention

A testing apparatus for testing the level of retained carbon dioxide in containers according to the present invention includes engaging means for engaging an opening in said containers, the opening typically being a mouth of the container. The apparatus additionally includes gas supply means for supplying a desired quantity of a selected gas to each container, the gas typically being carbon dioxide or helium, but other gases can be used. The apparatus further includes pressure measuring means for measuring the pressure in each container, and data collection means coupled to the pressure measuring means for periodically collecting pressure data as a function of time. Ambient temperature is also measured.

The container shelf life evaluation is carried out by a series of steps including mounting a plurality of containers to the container engaging means so that they are hermetically engaged, purging any air from within the containers with a selected gas, and charging the containers to a selected volume specification with the selected gas. Thereafter the evaluation is carried out by individually isolating each of the plurality of containers, instrumenting each container with a pressure measuring means, coupling a data gathering unit to the pressure measuring means, periodically collecting data from each of the pressure measuring means, and storing the collected values thereof for analysis along with the ambient temperature values.

A testing unit according to the present invention is preferably a completely automated system where containers are purged of air with pure $CO_2$ gas and then charged to a selected volume specification with pure $CO_2$ gas, only achieving the same molar concentration of $CO_2$ as with standard carbonated water methods. The containers are mounted to threaded aluminum manifolds with rubber seals to prevent leakage and each manifold station has an individual shutoff valve and pressure transducer. Once each container is mounted to its individually isolated and instrumented manifold station, a PC based computer system periodically monitors the container pressures and room temp of a custom designed multiplexer and stores the values in a spreadsheet for future analysis.

An advantage of the apparatus of the present invention is the elimination of the use of carbonated water to perform the test as it has been observed that the test results using pure $CO_2$ gas yield nearly the same results. A further advantage of the present invention lies in the substitution of helium gas for the pure $CO_2$ gas as the substitution allows for valid test results to be achieved much more quickly. The invention also automates the testing, minimizes temperature sensitivity, and eliminates physical measurement inaccuracies thereby arriving at more reliable results with less expenditure of manpower.

Additional features and advantages of the present invention will become apparent to those skilled in the art upon consideration of the following description, which when taken in conjunction with the drawings, sets forth the preferred embodiment of the present invention. The embodiment of the invention disclosed herein is the best mode contemplated by the inventors for carrying out the invention in a commercial environment, although it should be understood that various modifications can be accomplished within the parameters of the present invention.

BEST MODE OF CARRYING OUT THE INVENTION

Figure 1:
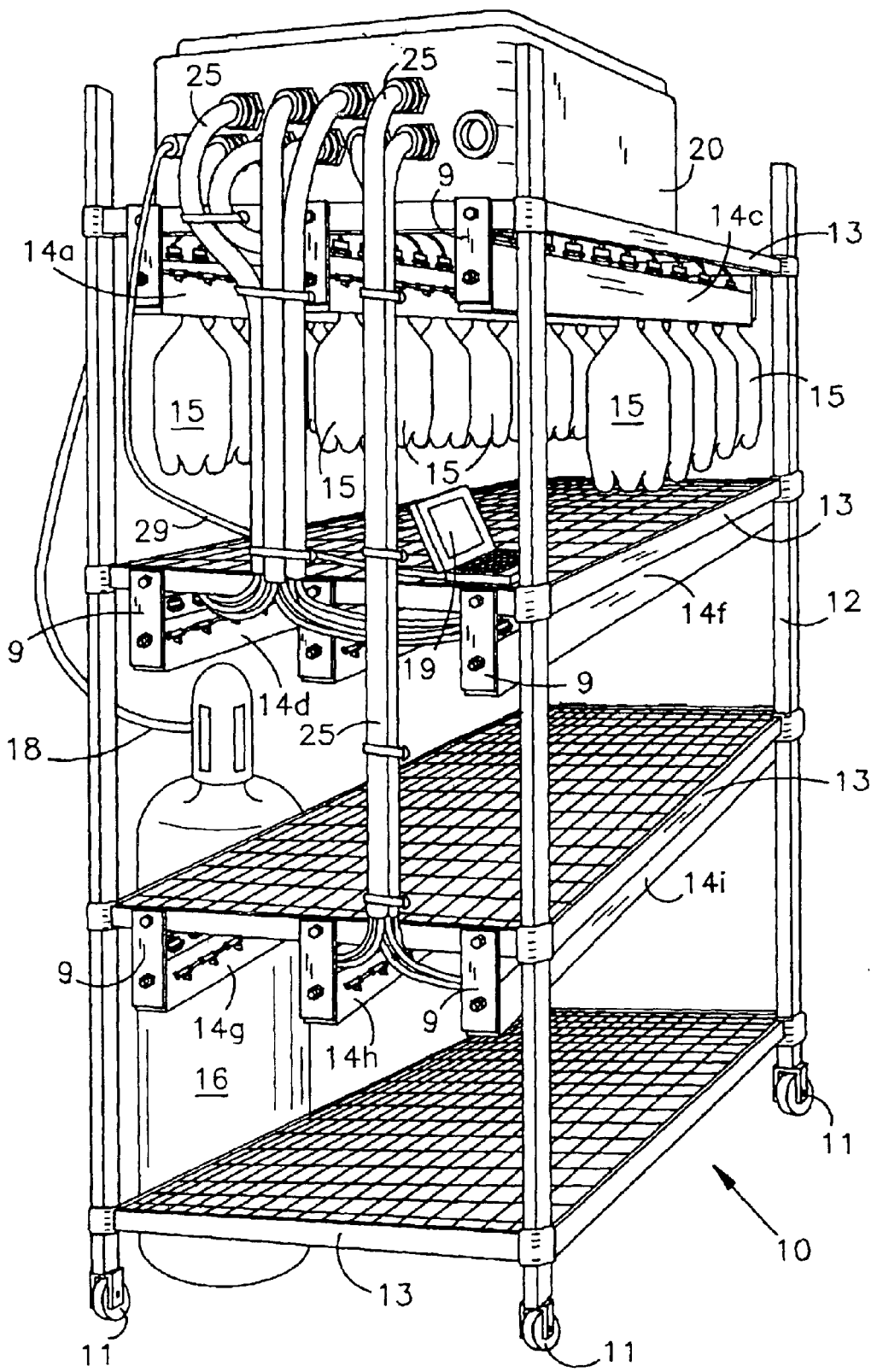
FIG. 1 is a perspective view of a shelf life testing apparatus according to the present invention.
Figure 2:
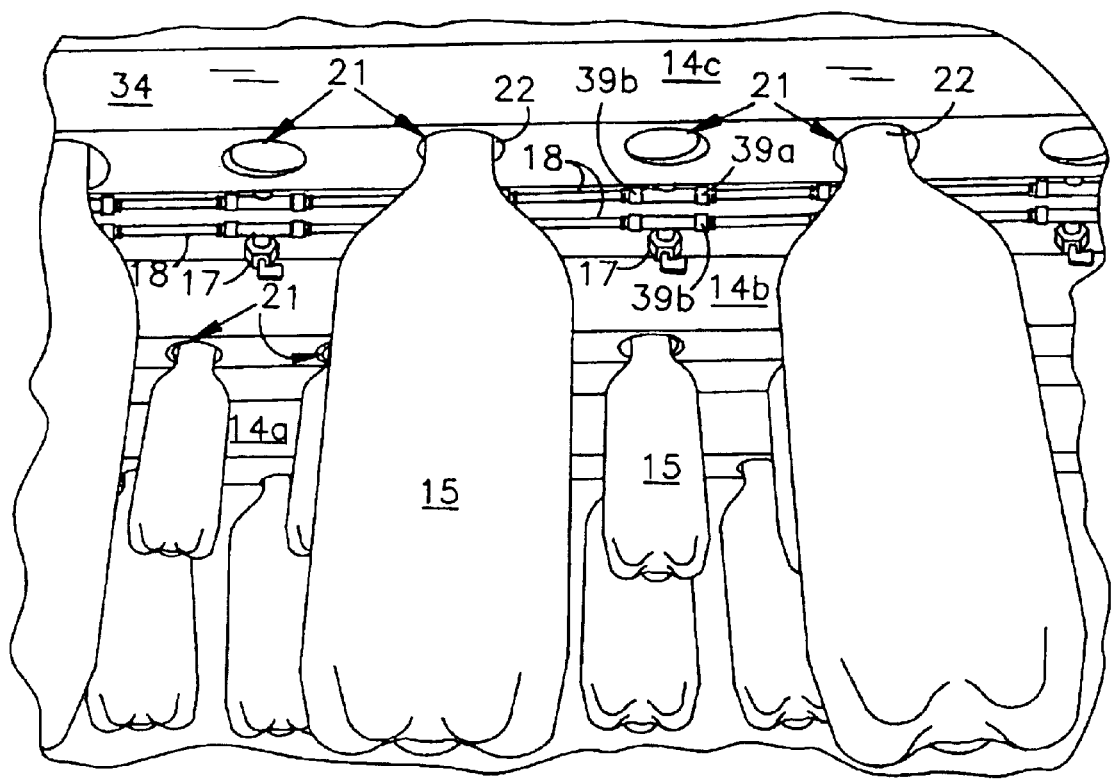
FIG. 2 is a partial front view of the apparatus shown in FIG. 1 showing one possible arrangement of containers on the apparatus.
Figure 3:
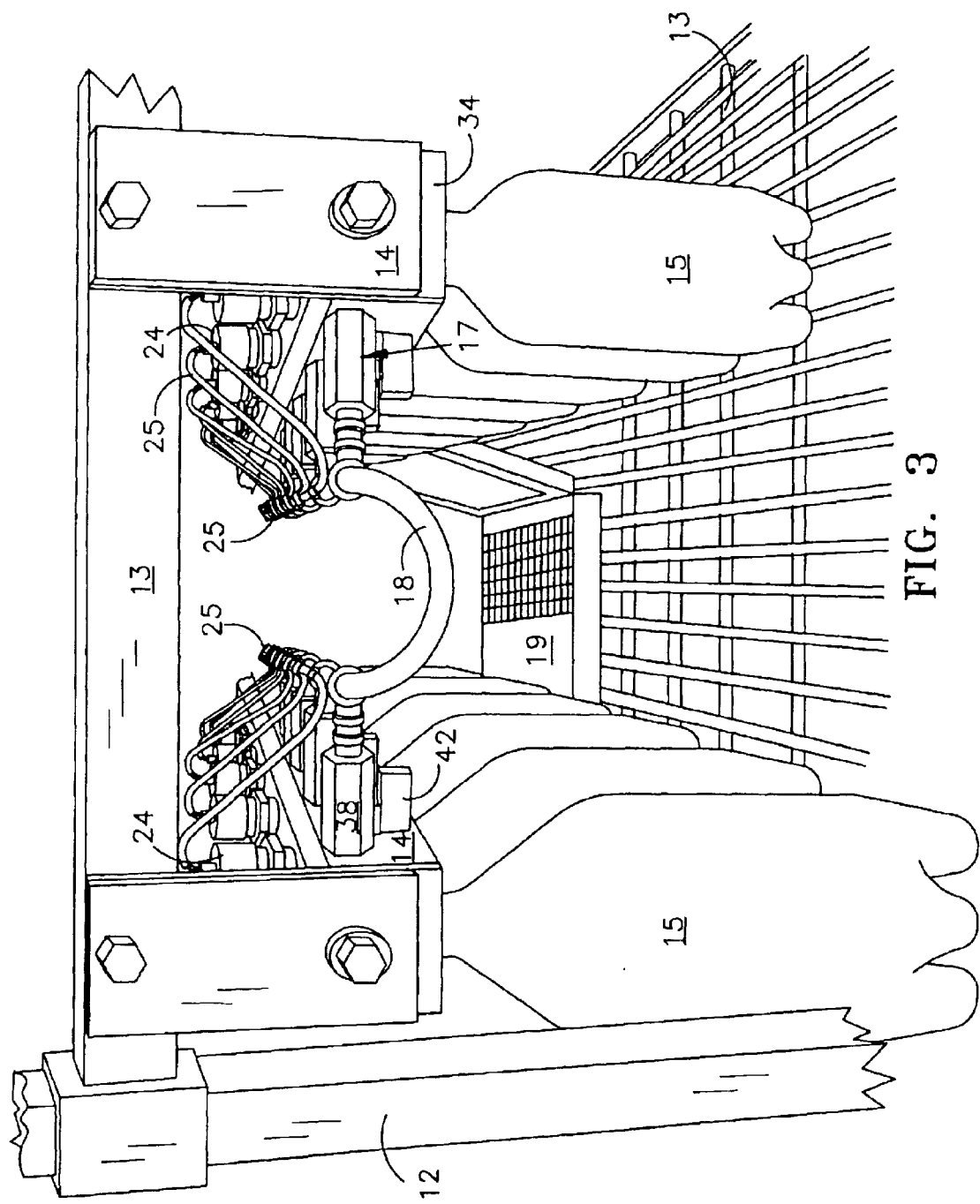
FIG. 3 is a partial end view of the apparatus showing the valve, transducer and manifold arrangement of the apparatus.

A shelf life testing apparatus 10 according to the present invention is shown in FIGS. 1–3 to generally comprise a stand 12. The stand 12 is preferably mounted on wheels 11 so as to be mobile to permit ease of movement of the testing apparatus 10 from one environment to another, e.g., rooms having widely different temperatures. The stand 12 includes several shelves 13a–13d supporting a plurality of manifold assemblies 14a–14i by brackets 9 suspended below each shelf 13. Each manifold assembly 14 is connected to a source of gas 16 through a conduit 18. A plurality of containers 15 can be attached to each of the manifold assemblies 14 for testing in accordance with the methods of the present invention. While FIG. 1 shows containers 15 being coupled to only the manifold assemblies 14a–14c that are supported by the top shelf 13a, it will be appreciated that the remaining manifold assemblies 14d–14i are similarly capable of being attached to such containers, and that the containers have been omitted to simplify the illustration.

Figure 4:
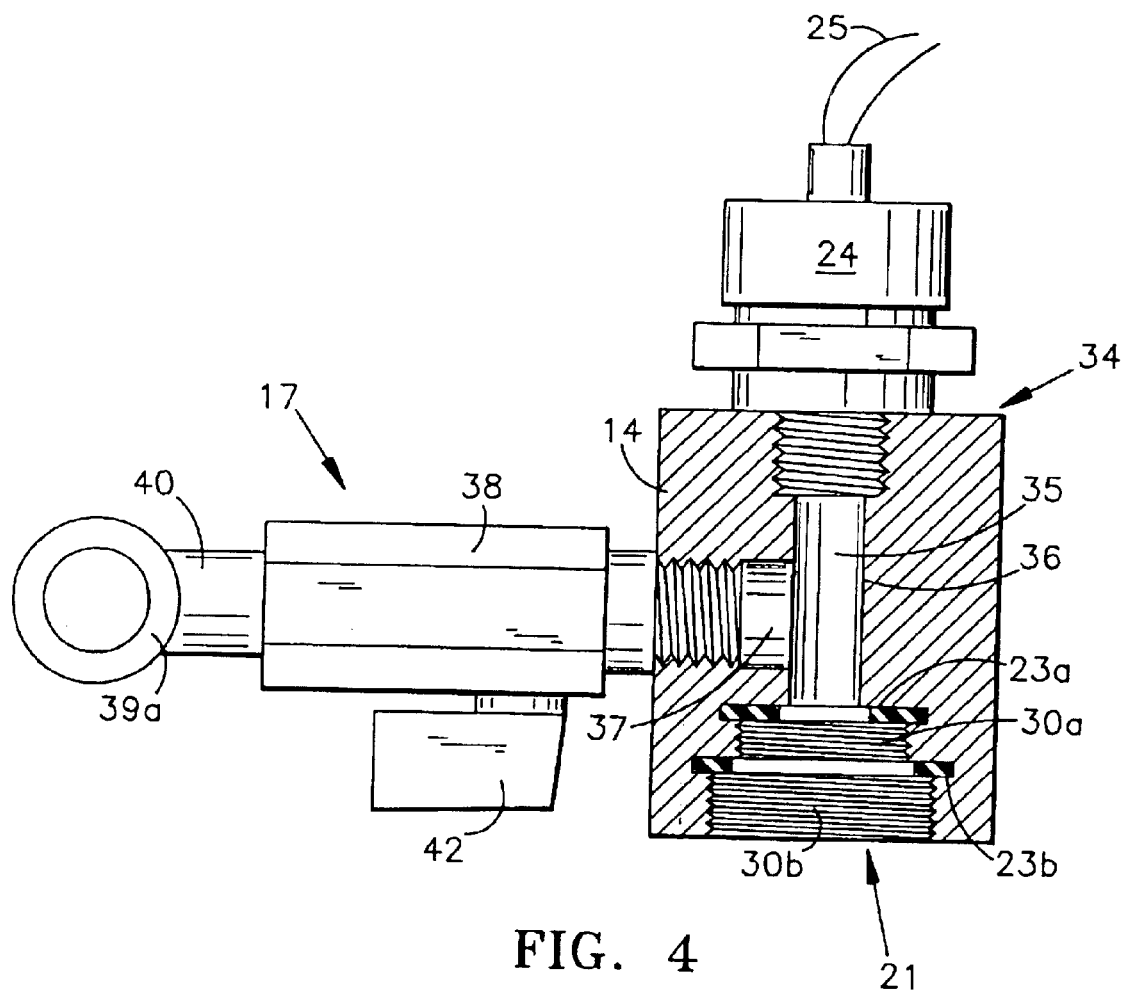
FIG. 4 is a sectional view of the valve, transducer and manifold arrangement shown in FIG. 3.
Figure 5:
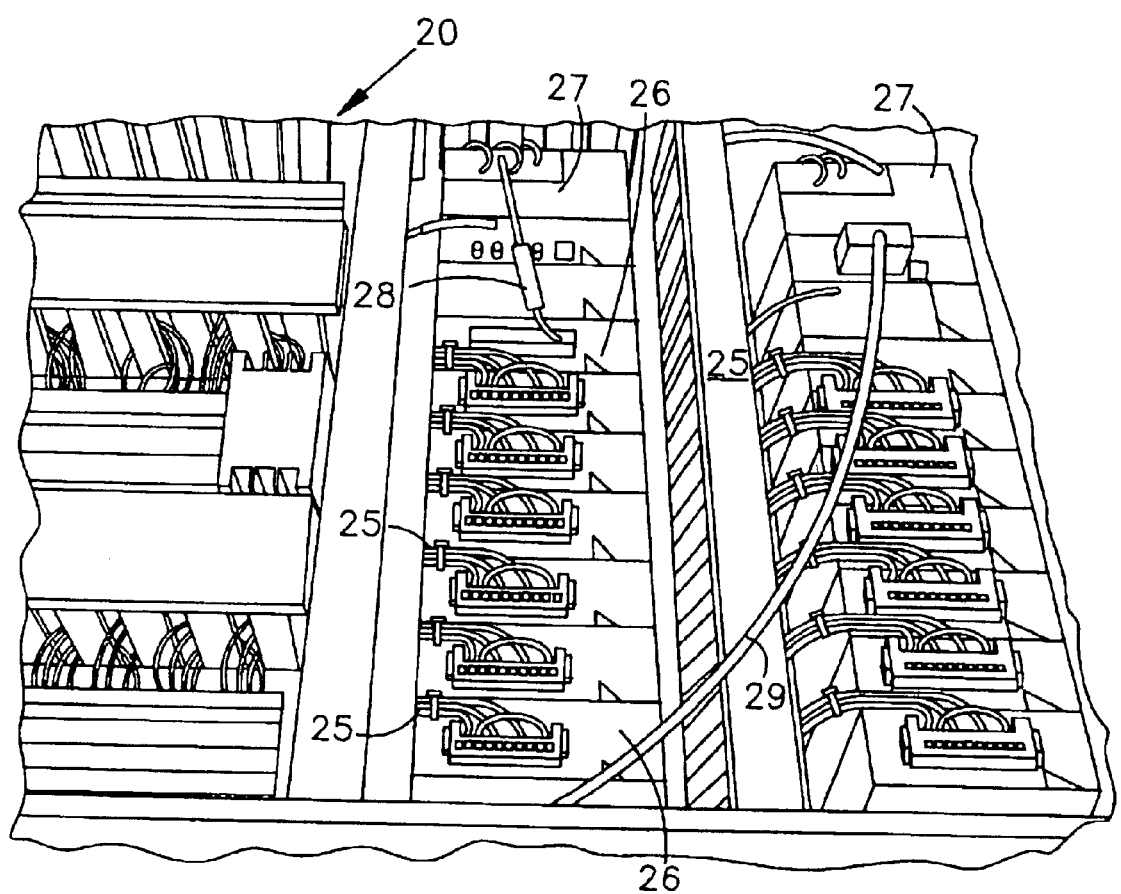
FIG. 5 is a plan view of the data gathering multiplexer.

Valves 17, shown in FIGS. 2–4, couple the conduit 18 to the manifold assemblies 14. Preferably, the valves 17 control the supply of gas from source 16 so that each container 15 can be individually supplied with a desired quantity of gas from the source 16 at the initiation of testing. The source of gas 16 is generally a typical commercial tank containing the gas at super atmospheric pressure, the tank having an outlet, a variable pressure reducing valve having an inlet coupled to the tank outlet and a valve outlet coupled to line 18 leading to the plurality of valves 17. The gas preferably employed is helium rather than carbon dioxide as will become evident from the later disclosure of certain qualifying tests that have been conducted. While it may be possible to employ other gases, helium is generally readily available and is safe to use in a wide variety of situations in which other gases might present a hazard. The stand 12 also supports a data gathering unit 20 that can be coupled to a standard PC computer 19 for periodically gathering data of the internal pressures of each of the containers 15 along information on the environment to which the containers 15 are exposed.

Each manifold assembly 14a–14i includes an elongated bar 34 having a plurality of openings 21, shown in FIGS. 2 and 4 that are threaded to receive the finish portion 22 of a number of containers 15. In the preferred embodiment, each of the openings 21 in bar 34 includes a standard 28 mm thread 30a located coaxially within a standard 38 mm thread 30b, as shown in FIG. 4, so that either convention opening or wide mouth opening containers can be tested on the same unit. Seals 23a and 23b, preferably made of rubber, seal each of the containers 15 in each opening 21 to prevent any leakage. In the preferred embodiment the openings 21 are spaced, as best shown in FIG. 2, so that conventional 20-ounce or 1-liter soft drink bottles can be received in close adjacency along the length of the manifold assembly 14, for example as shown on manifold assembly 14b. In the preferred embodiment the openings 21 are spaced so that conventional 2-liter soft drink bottles can be received in spaced adjacency with an intervening unused opening 21 as shown in conjunction with manifold assemblies 14a and 14c.

As shown in detail in FIG. 4, each opening 21 leads to a generally T-shaped interior channel 36 consisting of a vertical portion 35 and a horizontal portion 37. One of the valves 17 is coupled to an open end of the horizontal channel 37. Each valve 17 includes a valve body 38 that has a first end that threaded, braised, or otherwise coupled to one of the a horizontal channels 37 in bar 34. A T-shaped coupling 40 having laterally extending portions 39a and 39b is connected to the other end of the valve body 38. The two laterally extending portions 39a and 39b are coupled to conduit 18, which is in turn coupled to the source of gas 16. Each valve body 38 includes a stem 41 that can be manipulated by handle 42 to control the amount of gas that is admitted through interior channel 36 into a corresponding container 15 that is secured to opening 21. The individual valves 17 permit the use of any number of the openings 21 to be connected to containers 15. The gas can be introduced into each container individually or into several containers at one time.

In a preferred procedure, a container is loosely engaged into one of the threaded portions 30a or 30b, and the corresponding valve 17 is opened to permit gas to flow downward into the container through the vertical portion 35 of channel 36. The downward flow of gas entering through the channel 36 causes a flushing action to occur, which forces the air in the container out through the loose fitting between the container finish and the corresponding thread. After a suitable time has passed that will ensure the container is occupied by only the desired gas, typically about 10 seconds, the container is engaged tightly with the corresponding thread so that an upper lip of the container seals against one of the seals 23a or 23b. When an entire set of containers have been suitably engaged, the pressure within the entire set is raised to the initial test pressure by manipulating the pressure in conduit 18 by a pressure control valve at the gas source 16. When a suitable pressure is reached in all containers, all of the valves 17 are closed to isolate each container 15 from all other containers. The containers can contain some liquid such as carbonated water, but as will be seen below, such liquids are preferably omitted.

A pressure transducer 24 is secured by being threaded or braised to communicate with the upper end of each vertical channel 35 for individually monitoring the pressure within each container 15. A cable 25 couples each pressure transducer 24 to the data gathering unit 20. The data gathering unit 20 contains a plurality of multiplexers 26 that can periodically poll the pressure sensed by each of the pressure transducers. The multiplexers 26 preferably take the form of Siemens or Koyo PLC Direct 205 series programmable controllers 27 controlled by the PC based computer 19. The information collected by the controllers 27 is generally collected on a periodic basis and delivered to the computer 19 through a suitable serial or parallel port by cable 29. The ambient temperature in the area of the test unit 10 is also recorded with an electronic temperature sensor 28. Using a control program, such as AIMAX® for Windows®, the data on pressure and temperature is collected in a conventional spread sheet format, such as Excel®, for later analysis.

To ensure the reliability of the apparatus 10, a study was undertaken using 2-liter and 20-oz carbonated soft drink containers to determine whether the data gathered by the apparatus are container size independent. Both groups of containers were manufactured in production facilities and sample sets were tested as described below:

Test 1: A first set of containers were filled with carbonated water and tested using Pepsin standard shelf life procedures, generally in accord with ASTM Standard F 1115-95, but at 1-week intervals.

Test 2: A second set of the same groups of containers were filled with carbonated water and tested using the apparatus of the present invention.

Test 3: A third set of the same groups of containers were filled merely with $CO_2$ gas and tested using the apparatus of the present invention.

Test 4: A forth set of the same groups of containers were filled with $CO_2$ gas and tested on a schedule similar to the first group.

Test 5: A fifth set of the same groups of containers were filled with Helium gas and tested using the apparatus of the present invention.

A first series of tests 1–5 were performed on sets of 2-liter bottles. In the following tables, the apparatus and methods of the present invention are symbolized by the abbreviation SLTU while the Pepsi® standard shelf life procedures, generally in accord with ASTM Standard F 1115-95, are symbolized by the abbreviation "Regular".

Table 1 below shows the quantities of bottles in each 2-liter set:

TABLE 1

| Test Method and Number | | Initial Sample Size | Final Sample Size |
|---|---|---|---|
| Regular - Carb. Water | #1 | 30 | 27 |
| SLTU - Carb. Water | #2 | 10 | 9 |
| SLTU - $CO_2$ Gas | #3 | 9 | 8 |
| Regular - $CO_2$ Gas | #4 | 30 | 30 |
| SLTU - Helium Gas | #5 | 10 | 7 |

Figure 6:
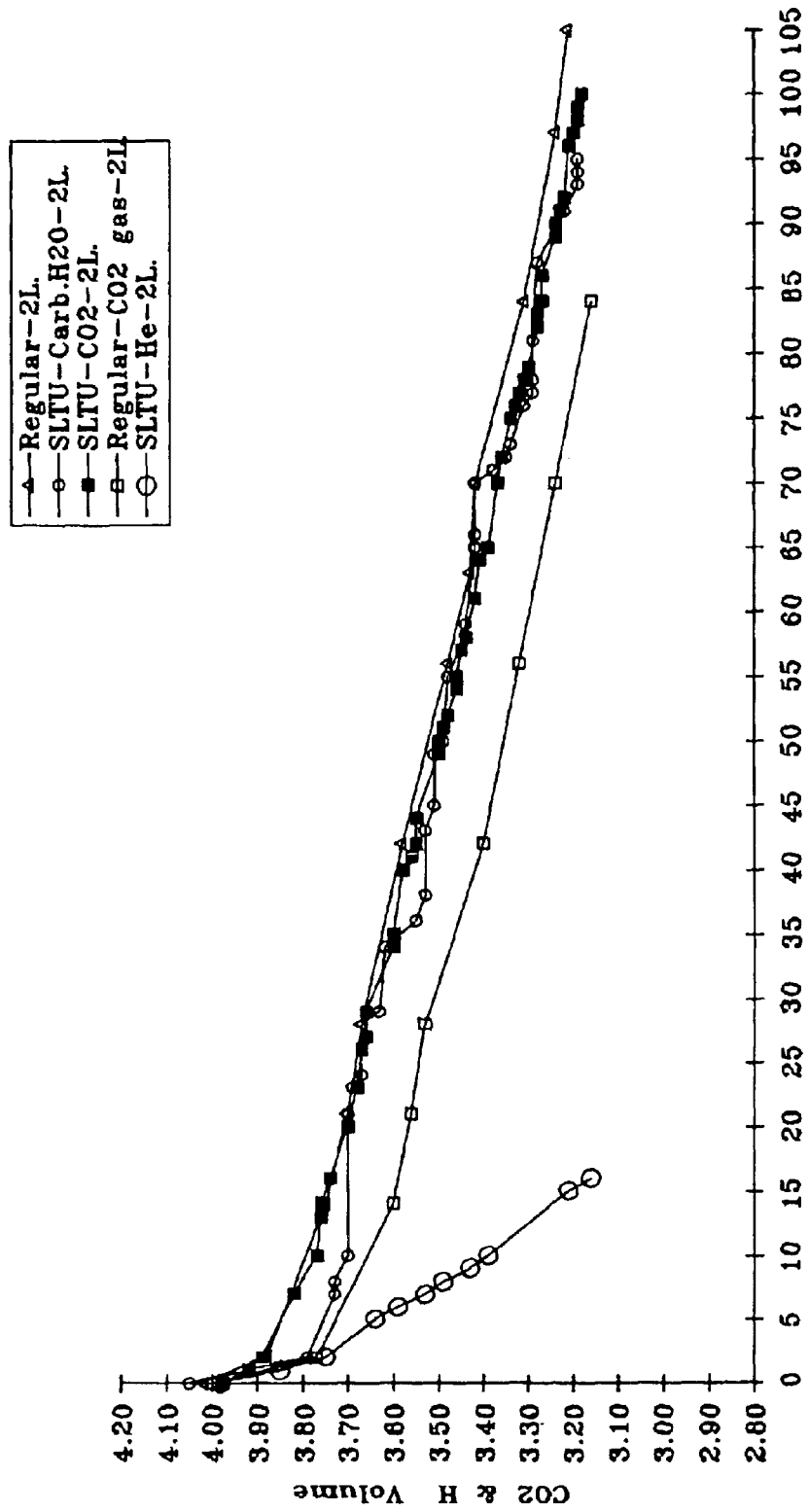
FIG. 6 is a graph of the $CO_2$ and He concentration, measured in volumes, over time for containers having an internal volume of 2 liters.

In each test, the data gathered at each point in time was averaged for all containers being tested in a given test and the mean values for each test sample were recorded. The results for the 2-liter tests are summarized in the chart shown in FIG. 6 wherein the curves are identified by the corresponding test numbers. An inspection of the curves in FIG. 6 shows a poor correlation between the Regular shelf life testing procedures using carbonated water (Test 1) and the same Regular shelf life procedures with bottles filled only with pure $CO_2$ (Test 4). Therefore, test procedure 4 is considered to be a non-viable alternative test method. By contrast, good correlation is observed between curves 1 through 3, and analytical comparisons of the three tests are presented in Table 2.

TABLE 2

| Test Method | Days to 15% loss | Percent Difference |
|---|---|---|
| Regular - Carb. Water #1 | 71 | N/A |
| SLTU - Carb. Water - #2 | 64 | 9.9 |
| SLTU - $CO_2$ - Test #3 | 67 | 5.6 |

Surprisingly, the correlation between the Regular shelf life test was highest with the procedure of the present invention omitting the carbonated water. The absence of the carbonated water makes the test much easier to conduct as large supplies of carbonated water can be omitted. The omission of the carbonated water also reduces the physical strain experienced by the testing personnel, which no longer have to be handling large numbers of containers filled with liquid.

The ratio between the SLTU-$CO_2$ Test Method results and the Helium results, Test #5, at 15% loss is shown below in Table 3. The test method employing helium closely approximates the results obtained by Test #3 except for a ratio reflecting the difference in permeability of the two gasses employed as both systems experience diffusion in a similar manner. Sensitivity to temperature variations is much less with the inventive methods than with the Regular Test Method, and is particularly diminished in the helium method. Importantly, the helium test is much to be preferred since it can be conduced in about $\frac{1}{7}^{th}$ the time due to the much higher permeability of the helium.

TABLE 3

| Test Method | Days to 15% loss | SLTU - CO2/Helium |
|---|---|---|
| SLTU - CO2 - Test #3 | 67 | N/A |
| SLTU - Helium - Test #5 | 10 | 6.7 |

Figure 7:
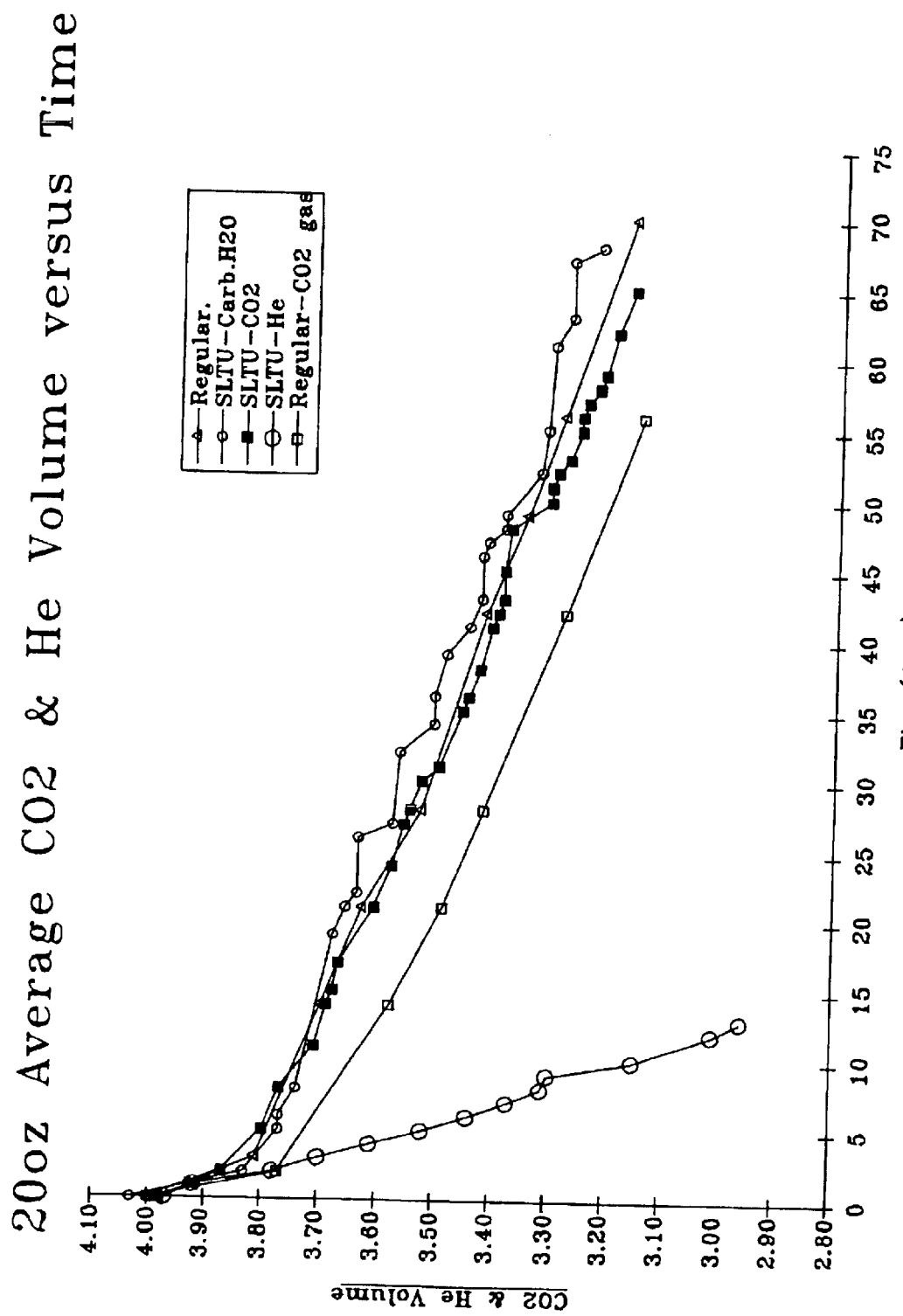
FIG. 7 is a graph of the $CO_2$ and He concentration, measured in volumes, over time for containers having an internal volume of 20 oz.

A second series of tests, numbered 6–10, similar to tests 1–5, were performed on sets of 20 oz bottles. Again, in the following tables, the apparatus and methods of the present invention are symbolized by the abbreviation SLTU while the Pepsi® standard shelf life procedures, generally in accord with ASTM Standard F 1115-95, are symbolized by the abbreviation "Regular". The results for the 20 oz tests are summarized in the chart shown in FIG. 7. Table 4 below shows the quantities of bottles used in each 20 oz. Test set:

TABLE 4

| Test Method and Number | | Initial Sample Size | Final Sample Size |
|---|---|---|---|
| Regular - Carb. Water | #6 | 29 | 18 |
| SLTU - Carb. Water | #7 | 10 | 10 |
| SLTU - $CO_2$ Gas | #8 | 10 | 10 |
| Regular - $CO_2$ Gas | #9 | 30 | 30 |
| SLTU - Helium Gas | #10 | 10 | 10 |

Inspection of the curves in FIG. 7 again show poor correlation between the Regular shelf life testing procedures and the Regular shelf life procedures (needle pressure gage and septum cap) with bottles filled only with pure $CO_2$. Therefore, test procedure 9 is also considered to be a non-viable alternative test method for 20 oz containers just as in the 2-liter container situation. Good correlation is observed between curves 6 through 8. Analytical comparisons are presented here in Table 5:

TABLE 5

| Test Method and Number | | Days to 15% loss | Percent Difference |
|---|---|---|---|
| Regular | #6 | 44 | N/A |
| SLTU - Carb. Water | #7 | 47 | 6.8 |
| SLTU - $CO_2$ | #8 | 47 | 6.8 |

The ratio between the SLTU-$CO_2$ Test Method results and the Helium results at 15% loss is shown below in Table 6.

TABLE 6

| Test Method and Number | | Days to 15% loss | SLTU - CO2/Helium |
|---|---|---|---|
| SLTU - $CO_2$ | Test #8 | 47 | N/A |
| SLTU - Helium | Test #10 | 7 | 6.7 |

The results indicate that the apparatus of the present invention using only pure $CO_2$ gas provides nearly identical results as the Regular test method using carbonated water with errors less than 7%, which translates to an error in shelf life measurement of less than 1 week for 2-liter and 3 days for 20 oz. This error can be attributed to the smaller sample size for the SLTU, less pronounced temperature effects with the SLTU method, and the recognized repeatability of any sample set with a certain tolerance range. The excellent agreement between SLTU-Carbonated Water (Test 7) and SLTU-$CO_2$ (Test 8) gas results indicate that the methods of the present invention are more repeatable than the Regular Shelf Life Testing Method. Additionally, the Helium tests 5 and 10 show consistent ratios of permeation rates with $CO_2$ of 6.7 times at both 20 oz and 2 L sizes. Therefore, the Helium to $CO_2$ permeation rates are constant and are independent of container size and geometry. Thus, the Helium permeation method allows accurate verification of $CO_2$ permeation rates in only about $\frac{1}{7}^{th}$ the time for a normal shelf life test. This translates to test durations lasting only about 1½ weeks for 2 liter containers and 1 week for 20 oz containers. This translates into faster new product qualification and quicker reliable product quality testing.

What is claimed is:

1. Apparatus for testing the duration of elevated pressure retention in a plurality of containers comprising: an assembly including engaging means for engaging an opening in each of the plurality of containers, gas supply means for supplying a desired quantity of a selected gas to each container through the engaging means, pressure measuring means coupled to the engaging means for measuring the pressure in each container, and data collection means coupled to the pressure measuring means for periodically collecting pressure data as a function of time to measure shelf life of the containers.

2. The apparatus of claim 1 wherein the assembly including engaging means comprises a manifold having a plurality of openings, each opening having one end including a dual threaded portion adapted to receive containers having openings of differing size.

3. The apparatus of claim 1 wherein the gas supply means comprises a common gas source coupled to all of the plurality of containers and a plurality of valves, each valve being coupled between the common gas source and only one of the plurality of containers so that each of the containers can be independently isolated from the common gas source.

4. The apparatus of claim 1 wherein the pressure measuring means comprises a plurality of transducers, each transducer being coupled through the engaging means to only one of the plurality of containers so that the pressure within each container can be measured in isolation from all other containers forming said plurality of containers.

5. The apparatus of claim 1 wherein the data collection means comprises a multiplexer coupled to the pressure measuring means of the plurality of containers and a computer programmed to periodically poll through the multiplexer pressure in each container as measured by the pressure measuring means, the computer being adapted to store the polled values for each container and to compute the mean of the values collected for determining the overall performance of the plurality of containers.

6. Apparatus for testing the duration of elevated pressure retention in at least one set of containers comprising: a manifold assembly having a plurality of openings adapted to receive a plurality of containers for testing, a source of gas connected to the manifold assembly including a plurality of valves connected between the source of gas and the openings for individually controlling the admission of gas to each container, a plurality of pressure transducers coupled to the manifold assembly, each transducer being in communication with only a single one of the containers, and a data gathering unit coupled to the pressure transducers for periodically collecting pressure data that can be evaluated to measure shelf life of each set of the containers.

7. The apparatus of claim 6 wherein the manifold assembly comprises a bar containing a plurality of channels, each channel leading to an opening configured to accept a mouth portion of a container to be tested, each channel also having an inlet connected to one of the plurality of valves, and an inlet connected to one of the plurality of pressure transducers.

8. The apparatus of claim 7 wherein each opening of the manifold assembly includes two threaded portions of differing diameter adapted to accept containers having correspondingly differing mouth diameters, and a seal in each threaded portion to prevent leakage between the manifold assembly and any container mounted thereto.

9. The apparatus of claim 7 wherein each of the pluralities of channels includes a horizontal portion coupled to one of the plurality of valves and a vertical portion for directing any incoming flow of gas from the source downward into any container coupled to the mouth portion so as to flush any undesired gas from the container by replacing the undesired gas with gas from said source of gas.

10. The apparatus of claim 6 further comprising a temperature measuring means coupled to the data gathering unit for measuring ambient temperature in the vicinity of the apparatus.

11. The apparatus of claim 6 wherein the source of gas comprises a tank containing the gas at super atmospheric pressure, the tank having an outlet, a variable pressure reducing valve having an inlet coupled to the tank outlet and a valve outlet coupled to a line leading to said plurality of valves.

12. The apparatus of claim 11 wherein the gas within the tank consists essentially of helium.

13. The apparatus of claim 6 wherein the data gathering unit comprises a multiplexer coupled to the pressure transducers, and a computer programmed to periodically poll through the multiplexer each value measured by the pressure transducers, each of the values measured being stored by the computer for analysis.

14. The apparatus of claim 6 wherein the data gathering unit includes a computer for storing the pressure data for evaluation of any loss of pressure as a function of time to establish an acceptable shelf life of the containers being tested.

15. The apparatus of claim 6 wherein the plurality of openings are spaced from each other by a distance of about 6 cm.

16. A method for evaluating the shelf life of a set of containers comprising the steps of mounting a plurality of containers to a manifold assembly connected to a source of a selected gas, purging any air from within the containers with the selected gas, charging the container to a selected initial pressure with the selected gas, individually isolating each of the plurality of containers from the source of gas and from each other, instrumenting each container with a pressure transducer, using a data gathering unit coupled to the pressure transducers to periodically collect pressure data from each of the transducers, and computing the mean pressure retention performance of the set of containers as a function of time to establish the shelf life.

17. The method of claim 16 wherein the selected gas consists essentially of helium and the periodic collection of pressure data is conducted for less than two weeks.

18. A system for evaluating the shelf life characteristics of groups of containers, each group of containers comprising a plurality of containers having a common geometry, the system comprising a unit having a set of manifolds, each manifold having a plurality of openings, each opening having one end including a dual threaded portion adapted to receive containers having openings of differing size, a gas supply having a common gas source coupled to a line leading to all of the manifolds and a plurality of valves, each valve being coupled between the common gas source and only one of the manifold openings so that each group of containers can be independently pressurized from the source of gas and each of the plurality of containers within each group can be isolated from the common gas source and from the other containers in the group, pressure measuring transducers coupled to each manifold in communication with only one of the openings so that the pressure within each container can be measured in isolation from all other containers forming each group of containers, a multiplexer coupled to the pressure measuring transducers for periodically polling the transducers coupled to openings leading to each container group to obtain a value indicative of the pressure measured by the pressure transducers in each container of the group, and a computer being adapted to store the polled values for each container and to compute the mean of the values collected for each group to determine the overall performance of each group of containers.

19. The system of claim 18 wherein the source of gas comprises a tank containing substantially only helium at super atmospheric pressure, the tank having an outlet, a variable pressure reducing valve having an inlet coupled to the tank outlet and a valve outlet coupled to a line leading to said plurality of valves.

20. The system of claim 19 further comprising a plurality of channels in each manifold, each channel including a horizontal portion coupled to only one of the plurality of valves and a vertical portion for directing any incoming flow of gas from the source downward into any container coupled to either of the threaded portions so as to flush any undesired gas from the container by replacing the undesired gas with gas from said source of gas.

* * * * *